US00PP12605P2

(12) United States Plant Patent
Bartels

(10) Patent No.: US PP12,605 P2
(45) Date of Patent: May 7, 2002

(54) PHLOX PLANT NAMED 'BARFOURTEEN'

(75) Inventor: Gosen B. H. Bartels, Aalsmeer (NL)

(73) Assignee: Bartels Breeding, B.V., Aalsmeer (NL)

( * ) Notice: Subject to any disclaimer, the term of this patent is extended or adjusted under 35 U.S.C. 154(b) by 0 days.

(21) Appl. No.: 09/563,942

(22) Filed: May 4, 2000

(51) Int. Cl.[7] ..... A01H 5/00

(52) U.S. Cl. ..... Plt./320

(58) Field of Search ..... Plt./320

(56) References Cited

PUBLICATIONS

UPOV–ROM GTITM Computer Database, GTI JOUVE retrieval software 2000/02, citations for 'Barfourteen'.*

* cited by examiner

*Primary Examiner*—Bruce R. Campell
*Assistant Examiner*—Wendy C. Baker
(74) *Attorney, Agent, or Firm*—C. A. Whealy

(57) ABSTRACT

A distinct cultivar of Phlox plant named 'Barfourteen', characterized by its compact plant habit; suitability for potted plant production; freely and continuous branching; dense and bushy growth habit; and attractive and numerous dark reddish purple-colored flowers.

1 Drawing Sheet

BACKGROUND OF THE INVENTION

The present Invention relates to a new and distinct cultivar of Phlox plant, botanically known as *Phlox paniculata,* and hereinafter referred to by the cultivar name Barfourteen.

The new Phlox is a product of a planned breeding program conducted by the Inventor in Aalsmeer, The Netherlands. The objective of the breeding program was to create new compact Phlox cultivars suitable for potted plant production.

The new Phlox originated from a cross made by the Inventor of two proprietary selections of *Phlox paniculata* identified as code number 98.08 as the female, or seed, parent and code number 94.44.35.02 as the male, or pollen, parent. The new Phlox was discovered and selected by the Inventor in 1995 as a flowering plant within the progeny of the stated cross in a controlled environment in Aalsmeer, The Netherlands. The new Phlox was selected on the basis of its compact pot-type habit and attractive flower color.

Plants of the new Phlox differ from plants of the female parent selection primarily in flower color. Compared to plants of the male parent selection, plants of the new Phlox have a more compact plant habit.

Asexual reproduction of the new cultivar by terminal cuttings taken at Aalsmeer, The Netherlands, has shown that the unique features of this new Phlox are stable and reproduced true to type in successive generations.

SUMMARY OF THE INVENTION

Plants of the cultivar Barfourteen have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Barfourteen'. These characteristics in combination distinguish 'Barfourteen' as a new and distinct cultivar:

1. Compact plant habit, suitable for potted plant production; growth retardants are usually not required to maintain compact habit.
2. Freely and continuous branching; dense and bushy growth habit.
3. Attractive and numerous dark reddish purple-colored flowers.

Compared to plants of the *Phlox paniculata* cultivar 'Lilac Time', not patented, plants of the new Phlox have shorter lateral branches, shorter internodes and differ in flower color.

BRIEF DESCRIPTION OF THE PHOTOGRAPH

The accompanying colored photograph illustrates the overall appearance of the new cultivar, showing the colors as true as it is reasonably possible to obtain in colored reproduction of this type. Colors in the photographs may differ slightly from the color values cited in the detailed botanical description which more accurately describe the actual colors of the new Phlox. The photograph comprises a side perspective view of a typical flowering plant of 'Barfourteen'.

DETAILED BOTANICAL DESCRIPTION

In the following description, color references are made to The Royal Horticultural Society Colour Chart except where general terms of ordinary dictionary significance are used. Plants were grown in Aalsmeer, The Netherlands, in a glass-covered greenhouse and under field conditions which closely approximate commercial production conditions. Day temperatures ranged from 16 to 28° C. and night temperatures ranged from 10 to 18° C. Plants used for the description were about 12 weeks old.

Botanical classification: *Phlox paniculata* cultivar Barfourteen.

Parentage:

*Female parent.*—Proprietary selection of *Phlox paniculata* identified as code number 94.08, not patented.

*Male parent.*—Proprietary selection of *Phlox paniculata* identified as code number 94.44.35.02, not patented.

Propagation:

*Type cutting.*—Terminal vegetative cuttings.

*Time to initiate roots.*—Summer: About 21 days at 18° C. Winter: About 35 days at 18° C.

*Time to produce a rooted cutting or liner.*—Summer: About 28 days at 18° C. Winter: About 42 days at 18° C.

*Rooting description.*—Thick.

Plant description:

*Crop time.*—From cuttings, about 12 weeks are required to produce a finished flowering plant.

*Form.*—Compact; mostly upright; dense and bushy perennial. Plants typically do not require growth retardants to maintain compact growth habit.

*Usage.*—Appropriate for 13 to 17-cm containers.

*Plant height, soil level to top of plant plane.*—About 45 cm.

*Plant width.*—About 25 cm.

*Vigor.*—Low, slow growth rate.

*Branching habit.*—Freely branching with about ten lateral branches per plant; removal of terminal apices (pinching) enhances branching.

*Lateral branches.*—Length: About 10 cm. Diameter: About 8 mm. Internode length: About 2.5 cm. Texture: Smooth.

*Foliage description.*—Leaves simple, generally symmetrical and long persisting. Tolerant to stresses. Quantity per lateral branch: Typically about 20. Length: About 8 cm. Width: About 4 cm. Shape: Oblong elliptic. Apex: Sharply acute. Base: Rounded. Margin: Entire. Texture: Leathery; smooth. Color: Young foliage, upper surface: 144A. Young foliage, lower surface: 144A. Mature foliage, upper surface: 147B; venation, 147B. Mature foliage, lower surface: 138A; venation, 138A.

Flower description:

*Flower type and habit.*—Single rounded flowers arranged in terminal panicles; flowers face upright and outward. Panicles globular or pyramidal in shape. Freely flowering. Corolla, salverform, 5-lobed; calyx, five-cleft. Flowers last about four days on the plant. Not persistent.

*Natural flowering season.*—Continuously flowering from mid-summer through fall.

*Fragrance.*—Present, typical of species.

*Flower size.*—About 2 cm.

*Flower buds (just showing color).*—Length: About 1 cm. Diameter: About 5 mm. Shape: Elliptical. Rate of opening: About one day. Color: 144A.

*Petals.*—Arrangement/appearance: Single whorl of five petals, fused. Length: About 2.5 cm. Width: About 1 cm. Shape: Roughly deltoid. Apex: Rounded. Margin: Entire. Surface: Typically flat. Texture: Smooth. Color: Upper surface, when opening: 72A. Lower surface, when opening: 72A. Upper surface, opened flower: 72A; flower color doesn't fade. Lower surface, opened flower: 72A. Flower throat (inside): White, close to 155D. Flower tube (outside): 72A.

*Calyx.*—Shape: Campanulate; sepals, five, fused at base. Sepal shape: Narrowly deltoid; apex, acuminate; margin, entire. Texture: Smooth. Color, upper and lower surfaces: 144A.

*Pedicel.*—Strength: Strong. Angle: About 45° to the stem. Length: About 1 cm. Color: 145A.

*Reproductive organs.*—Stamens: Pollen amount: Scarce. Pollen color: 2D. Pistils: Pistil quantity per flower: One. Pistil length: About 2.5 cm. Stigma shape: Trilobate. Stigma color: 154D. Style color: 154D. Ovary color: 144A.

*Seed.*—Seed production has not been observed.

Disease tolerance: Plants of the new Phlox have been noted to be tolerant to Powdery Mildew under commercial production conditions.

It is claimed:

1. A new and distinct cultivar of Phlox plant named 'Barfourteen', as illustrated and described.

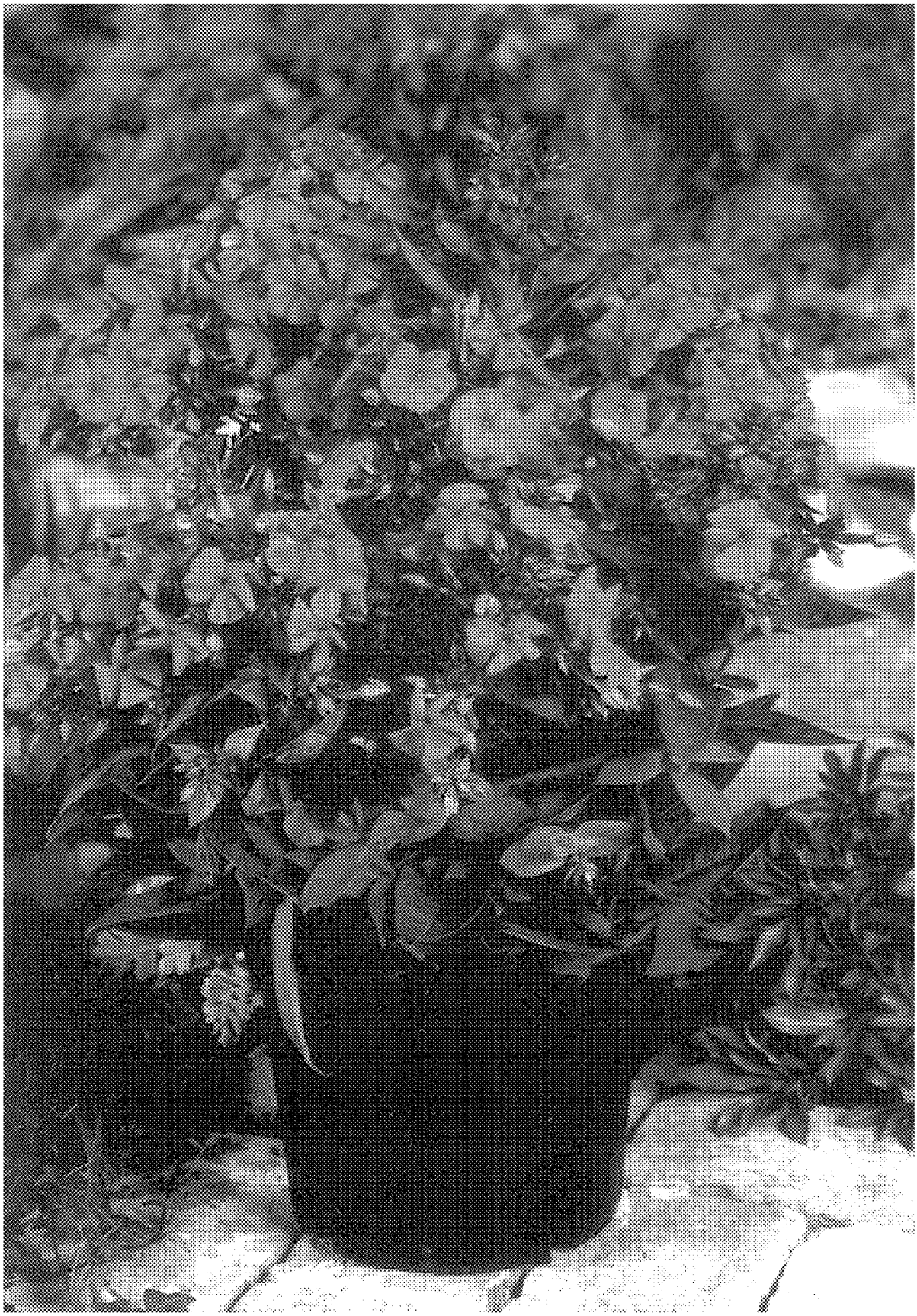

* * * * *